US006187787B1

(12) United States Patent
Gribble et al.

(10) Patent No.: US 6,187,787 B1
(45) Date of Patent: Feb. 13, 2001

(54) BIS(9-AMINOACRIDINE) DNA INTERCALATING AGENTS HAVING ANTITUMOR ACTIVITY

(75) Inventors: Gordon W. Gribble, Santa Cruz, CA (US); Gary D. Jaycox, West Chester, PA (US); Michael Mosher, Kearney, NE (US)

(73) Assignee: Trustees of Dartmouth College, Hanover, NH (US)

( * ) Notice: Under 35 U.S.C. 154(b), the term of this patent shall be extended for 0 days.

(21) Appl. No.: 09/446,171

(22) PCT Filed: Jun. 12, 1998

(86) PCT No.: PCT/US98/12309

§ 371 Date: Feb. 15, 2000

§ 102(e) Date: Feb. 15, 2000

(87) PCT Pub. No.: WO98/57956

PCT Pub. Date: Dec. 23, 1998

Related U.S. Application Data

(60) Provisional application No. 60/049,641, filed on Jun. 16, 1997.

(51) Int. Cl.[7] ................. A61K 31/473; C07D 401/08; C07D 401/10; C07D 401/12; A61P 35/02
(52) U.S. Cl. ............................................. 514/297; 546/106
(58) Field of Search ............................. 546/106; 514/297

(56) References Cited

U.S. PATENT DOCUMENTS

| 2,113,357 | 4/1938 | Mietzsch et al. | 260/36 |
|---|---|---|---|
| 2,441,665 | 5/1948 | Holcomb et al. | 260/279 |
| 2,503,899 | * 4/1950 | Britton | 260/279 |
| 5,783,584 | 7/1998 | Pang et al. | 514/297 |

OTHER PUBLICATIONS

National Cancer Institute Monograph 55. NIH Publication No. 80–1933, Dec. 1980.*

Gourdie et al., "Synthesis and Evaluation of DNA–Targeted Spatially Separated Bix (aniline mustards) as Potential Alkylating Agents with Enhanced DNA Cross–Linking Capability", *J. Med. Chem.* 1991 34:240–248.

Atwell et al., "A Diacridine Derivative That Binds by Bisintercalation at Two Contiguous Sites on DNA", *J. Am. Chem. Soc.* 1985 107:4335–4337.

Barbet et al., "DNA Polyintercalating Drugs. Proton Magnetic Resonance Studies of a New Acridine Dimer. Conformations and Interactions with Mono–and Dinucleotide", *Biochemistry* 1976 15:2642.

Becker and Dervan, "Molecular Recognition of Nucleic Acid by Small Molecules. Binding Affinity and Structural Specificity of Bix (methidiuum) spermine", *J. Am. Chem. Soc.* 1979 101:3664.

Canellakis et al., "Diacridines: Bifunctional Intercalators", *Biochim. Biophys. Acta*, 1976 418:277.

Capelle et al., "Deoxyribonucleic Acid Bifunctional Inercalators: Kinetic Investigation of the Binding of Several Acridine Dimers to Deoxyribonucleic Acid", *Biochemistry* 1979 18:3354.

Denny et al., "Potential Antitumor Activity of New Classes of Diacridines: Importance of Linker Chain Rigidity for DNA Binding Kinetics and Biological Activity", *J. Med. Chem.* 1985 28:1568.

Feigon et al., "Interactions of Antitumor Drugs with Natural DNA: $^1$H NMR Study of Binding Mode and Kinetics", *J. Med. Chem.* 1984 27:450.

Jaycox et al., "Potential DNA bis–Intercalating Agents: Synthesis and Antitumor Activity of Novel, Conformationally Restricted bis (9–Aminoacridines)", *J. Heterocyclic Chem.* 1987 24:1405–1408.

Le Pecq et al., "DNA polyintercalating drugs: DNA binding of diacridine derivatives", *Proc. Nat'l Acad. Sci. USA* 1975 72(8):2915–2919.

Wakelin et al., "Structural Limitations on the Bifunctional Intercalation of Diacridines into DNA", *Biochemistry* 1978 17:5057.

Wakelin et al., Polyfunctional DNA Intercalating Agents:, *Med. Res. Rev.* 1986 6:275.

Gennaro, Alfonso, Ed., Remington's Pharmaceutical Sciences, 18th Edition 1990. Mack Publishing Co., Easton, PA.

* cited by examiner

*Primary Examiner*—Evelyn Mei Huang
(74) *Attorney, Agent, or Firm*—Law Offices of Jane Massey Licata

(57) ABSTRACT

A series of bis-acridinyl DNA intercalating agents with anticancer cell activity represented by formula (I), where Z is a linear arrangement of multiple aromatic rings, containing at least three aromatic rings, or at least two alicyclic rings, said rings being linked in a 1,4 or 1,3 manner are provided. Methods of inhibiting cancer cells and treating patients having cancer with these agents are also provided.

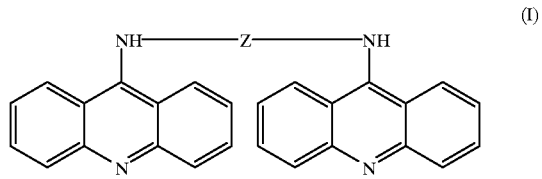

4 Claims, No Drawings

BIS(9-AMINOACRIDINE) DNA INTERCALATING AGENTS HAVING ANTITUMOR ACTIVITY

This application is the national phase of PCT/US98/12309, filed Jun. 12, 1998, which claims the benefit of provisional application No. 06/049,641 filed Jun. 16, 1997.

BACKGROUND OF THE INVENTION

Intercalation is one of several modes by which drugs interact with DNA wherein a planar portion of the drug is inserted in between adjacent stacked base pairs of a double stranded DNA. The intercalation process results in helix extension and unwinding of the DNA. Included within these drugs are antitumor agents, actinomycin D, adriamycin and daunomycin, as well as several drugs for treatment of parasitic disease including ethidium bromide, quinacrine, chloroquine and miracil D. U.S. Pat. No. 2,441,665 discloses a class of alkylene diamine derivatives which are valuable as antimalarial agents. U.S. Pat. No. 2,113,357 discloses basically substituted amino-acridine derivatives useful in treating blood parasites.

More recently, DNA intercalating ligands have been proposed for use in targeting alkylating agents to DNA by attachment of the intercalating ligand to the alkylating agent. Gourdie et al. *J. Med. Chem.* 1991 34:240–248.

Since the biological properties of these DNA intercalating drugs are believed to result from their binding, researchers have focused efforts on designing molecules that have a high affinity for DNA. Planar polycyclic aromatic molecules show a strong propensity to bind to DNA by intercalation. Jaycox et al. *J. Heterocyclic Chem.* 1987 24:1405–1408. In recent years, efforts to identify molecules with a greater affinity and selectivity for DNA have resulted in the development of bifunctional intercalating agents in which two intercalating ligands are bridged by a central linking chain. In general, enhanced binding is observed with molecules of this type. Canellakis et al. *Biochim. Biophys. Acta,* 1976 418:277; Becker and Dervan, *J. Am. Chem. Soc.* 1979 101:3664; and Wakelin et al. *Med. Res. Rev.* 1986 6:275. However, the chemical and physical nature of the linking chain has been found to play a major role in the binding process.

A homologous series of diacridines containing two 9-aminoacridine chromophores linked via a simple methylene chain were studied in order to investigate the minimum interchromophore separation required to permit bifunctional intercalation. Wakelin et al. *Biochemistry* 1978 17:5057. Viscometric, sedimentation and electric dichroism experiments showed that compounds having one to four methylene groups in the linker are restricted to monofunctional intercalation whereas bifunctional interaction was observed when the chain length was increased to six methylene groups or more. Accordingly, the transition in functionality was concluded to lie between interchromophore distances of 6.3 and 8.8 angstroms.

Additional studies however, indicate that the nature of the bridging chain and/or substituents on the acridine ring has a profound effect on the ability of diacridine compounds to act as bifunctional intercalating agents. DNA binding characteristics of a number of acridine dimers of which two aromatic rings, each ring being the monomeric 2-methoxy-6-chloro-9-(3-dimethyl amino propylamino acridine), were linked by a chain of varying length and structure were also determined. Le Pecq et al. *Proc. Nat'l Acad. Sci. USA* 1975 72(8):2915–2919. The linking chains of these acridine dimers include: —(CH$_2$)$_3$—NH—(CH$_2$)$_4$—NH—(CH$_2$)$_3$— (IIA); —(CH$_2$)$_3$—NH—(CH$_2$)$_4$ (IIB); and (CH$_2$)$_3$—NH—(CH$_2$)$_3$(III). It was found that the 2 dimers with the longest chain length, (IIA) and (IIB), bisintercalated while only one of the two rings of the dimer with the shortest chain (III) of 9 angstroms was intercalated. Bisintercalative binding of a bis(acridine) derivative specifically designed as a relatively rigid molecule in which the two chromophores are essentially coplanar and 7 angstroms apart in the only reasonably strain-free conformation has also been reported. Atwell et al. *J. Am. Chem. Soc.* 1985 107:4335–4337.

In contrast, bis-intercalators bridged by flexible chains have generally exhibited reduced affinities for DNA, in part because of self stacking interactions which compete with the binding process. Barbet et al. *Biochemistry* 1976 15:2642; and Capelle et al. *Biochemistry* 1979 18:3354. Further, bis-intercalation can introduce undesirable entropic effects when a flexible linker is forced into an extended chain conformation. Jaycox et al. *J. Heterocyclic Chem.* 1987 24:1405–1408. In addition, it is a concern that flexible bis-intercalators can creep in a stepwise fashion along the DNA macromolecule, thereby lowering ligand residence lifetimes at any one site. Denny et al. *J. Med. Chem.* 1985 28:1568. Such a process could have significant effects on efficacy of these intercalators as anticancer agents as residence lifetimes have been correlated with in vivo antitumor activity for a large number of DNA intercalators. Feigon et al. *J. Med. Chem.* 1984 27:450. Studies by Jaycox et al. indicate that it is the rigid tether framework and not the aromatic character of the linking chain that is responsible for the cytotoxic action of DNA intercalating agents. *J. Heterocyclic Chem.* 1987 24:1405–1408.

In the present invention a series of novel bis-acridinyl DNA intercalating agents with semi-flexible linking chains have been prepared and demonstrated to be tight binders of DNA and to have antitumor activity.

SUMMARY OF THE INVENTION

An object of the present invention is to provide compounds of formula (I)

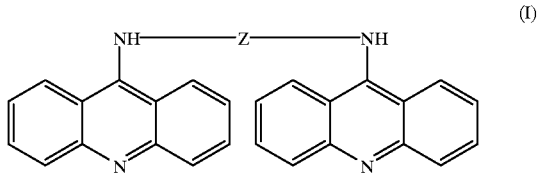

wherein Z comprises a linear arrangement of at least three aromatic rings or two acyclic rings arranged in a 1,4 or 1, 3 configuration.

Another object of the present invention is to provide a method of inhibiting cancer cells which comprised contacting the cells with a compound of formula (I).

Yet another object of the present invention is to provide a method of treating cancer in a patient which comprises administering to the patient an effective amount of a compound of formula (I) so that growth of the cancer is inhibited.

DETAILED DESCRIPTION OF THE INVENTION

A series of compounds have been synthesized which are represented by formula (I)

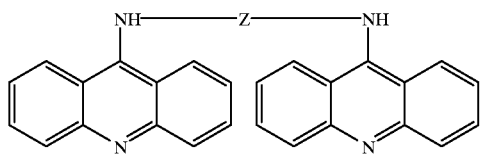
(I)

wherein Z comprises a linear arrangement of at least three aromatic rings or two acyclic rings arranged in a 1,4 or 1,3 configuration. In a preferred embodiment, Z is selected from a group consisting of

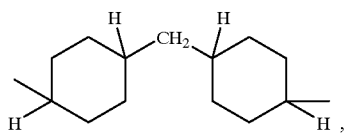

in either a cis—cis, cis-trans, or trans—trans configuration,

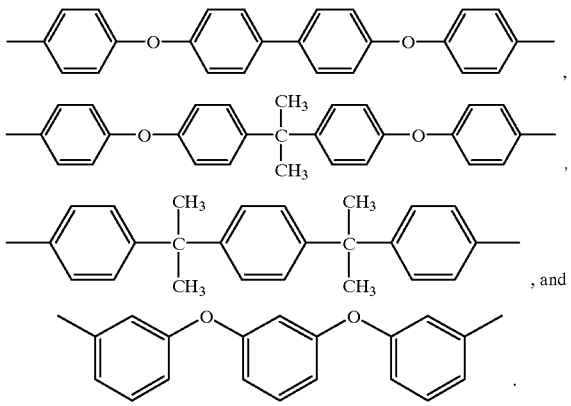
, and

U.S. Pat. No. 2,503,889 discloses halogenated diacridine compounds with similar linking chains.

The compounds of the present invention have been demonstrated to bind DNA in a tighter fashion than DNA intercalation agents currently in clinical use for the treatment of cancer. In addition, the compounds of the present invention have been demonstrated to be more effective inhibitors of cancer cells than bis(9-aminoacridines) disclosed in the prior art. Accordingly, it is believed that the compounds of the present invention will be useful in treating patients suffering from cancer.

In one embodiment, compounds of the present invention are synthesized from the condensation of 9-chloroacridine with selected diamines in a molten phenol solution and isolated via flash chromatography. Preferably, the diamine comprises the formula:

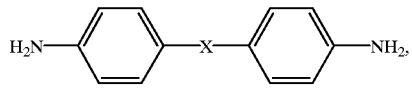

wherein X is either —O—, —$CH_2$—, —$CH_2$—$CH_2$—, or CH=CH. However, as will be obvious to those of skill in the art upon this disclosure, other means of synthesis can be used.

The compounds of the present invention were demonstrated to have increased DNA binding affinity. Thermal denaturation studies were performed on calf thymus DNA. Addition of the compounds of the present invention to the calf thymus DNA caused the denaturation temperature to increase approximately 11° C. (see Table 1).

Further, these compounds were demonstrated to have inhibitory activity against cancer cells. Using the methodologies disclosed by Jaycox et al. *J. Heterocyclic. Chem.* 1987 24:1405–1408, the compounds of the present invention were tested for their ability to exhibit cytotoxicity in the murine leukemia cell line (L1210). A number of intercalating agents currently in clinical use for treatment of cancer were also evaluated in this assay for comparison. ID50 values (the concentration which inhibits growth of 50% of the cells) for each compound are shown in Table 1.

TABLE 1

| WHEREIN Z IS: | $\Delta T_m$ | $ID_{50}$ ($\mu M$) |
|---|---|---|
| (cis-cis) | n.d. | 0.44 |
| (cis-trans) | n.d. | 0.56 |

TABLE 1-continued

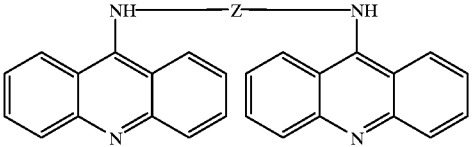

| WHEREIN Z IS: | ΔT$_m$ | ID$_{50}$ (μM)] |
|---|---|---|
| 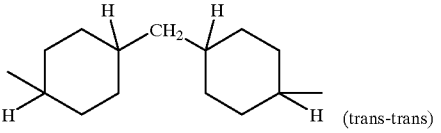 (trans-trans) | n.d. | 0.50 |
| 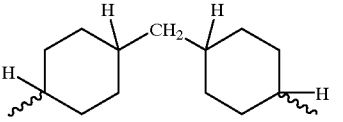 | 25.9 ± 4.1 | |
| 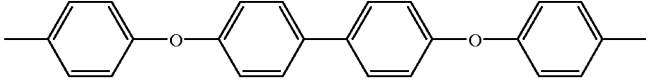 | n.d. | n.d. |
| 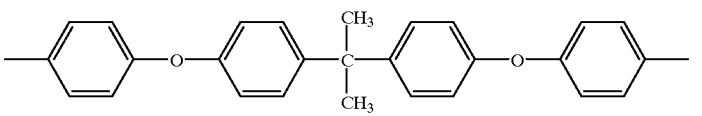 | 11.6 ± 0.4 | 5.4 |
| 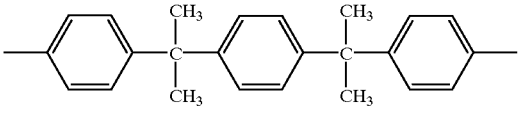 | 10.9 ± 0.31 | >13.0 |
| 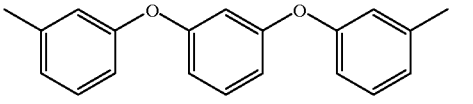 | n.d. | 5.9 |
| ellipticine | n.d. | 0.53 |
| ethidium bromide | n.d. | 4.1 |
| distamycin-A | n.d. | 6.0 |
| 5-methyl-1,10-phenanthroline | n.d. | 2.0 |
| 9-aminoacridine | n.d. | 2.3 |

Accordingly, it is believed that the compounds of the present invention will be useful in treating patients suffering from cancer.

The present invention thus also relates to methods of treating cancer in a patient wherein an effective amount of a compound of the present invention is administered to the patient so that growth of the cancer cells is inhibited. In a preferred embodiment, the compound is administered in a pharmaceutically acceptable carrier. Suitable pharmaceutically acceptable carriers are well known in the art and are described for example in Gennaro, Alfonso, Ed., Remington's Pharmaceutical Sciences, 18th Edition 1990. Mack Publishing Co., Easton, Pa., a standard reference text in this field. Pharmaceutical carriers may be selected in accordance with the intended route of administration and the standard pharmaceutical practice. In a preferred embodiment, an effective amount of compound of the present invention is administered to a patient intravenously or intratumorally and may be linked to a carrier which selectively targets tumor cells. By "effective amount" it is meant a concentration or dose of a compound of the present invention which will inhibit cancer cell growth. Such dosages can be calculated routinely by those of skill in the art in accordance with in vitro data provided herein and dosages used for other DNA intercalating agents in clinical use.

The following nonlimiting examples are provided to further illustrate the present invention.

EXAMPLES

Example 1

Preparation of -N,N'(4,4'-cis-cis-diaminodicyclohexyl methane)-bis-9-acridineamine A magnetically stirred solution of 4,4'-cis-cis-diaminodicyclohexyl methane (0.15 grams, 0.727 mmol) and 9-chloroacridine (0.51 grams, 2.39 mmol) was warmed at 65–75° C. in phenol (10 grams, 0.11 mole) for 24 hours. After being cooled to room temperature, the solution was treated with 0.1N sodium hydroxide (100 ml) and extracted with chloroform (3×100 ml). The chloroform extract was washed with water (5×100 ml) and brine (1×75 ml) and then dried over sodium sulfate. The solution was concentrated in vacuo to afford after flash chromatography (silica gel/95% ethyl ether, 5% triethylamine) a hygroscopic solid. The solid was crystallized from THF/hexane and dried in vacuo to yield 0.115 grams (28%) of a bright yellow powder, melting point 232–234° C. NMR, UV and elemental analytical data support the structural assignment.

Example 2

Preparation of -N,N'(4,4'cis-trans-diamino dicyclohexyl methane-bis-9-acridineamine Preparation was performed in analogous fashion to Example 1, condensing 4,4'-cis-trans-diaminodicyclohexyl methane (0.26 grams, 1.26 mmol) with 9-chloroacridine (1.08 grams, 5.05 mmol) to yield 0.56 grams (79%) of a bright yellow powder, melting point 197–198° C. NMR, UV and elemental analytical data support the structure assignment.

Example 3

Preparation of N,N'(4,4'-trans-trans-diamino-dicyclohexyl methane-bis-9-acridineamine Preparation was performed in analogous fashion to Example 1, condensing 4,4'-trans-trans-diamino-dicyclohexyl methane (0.36 grams, 1.74 mmol) with 9-chloroacridine (1.21 grams, 5.66 mmol) to yield 0.68 grams (70%) of a bright yellow powder, melting point 240–242° C. NMR, UV and elemental analytical data support the structure assignment.

Example 4

Preparation of N,N'(bis-4-oxy-4-phenylene) 4,4'-biphenyl-bis [9-acridineamine] . 2HCl To phenol (15 grams) was added, with stirring, 9-chloroacridine (1.082 grams, 5.06 mmol). The mixture was heated to 80° C. and BAPD (bis-(aminophenoxy) biphenyl) (0.42 grams, 1.14 mmol) was added. The orange reaction mixture turned a deep red color instantly upon addition of the diamine. The mixture was stirred for 5.5 hours at 85° C., then cooled to room temperature and triturated with ether (3×25 ml) to yield 1.04 grams (87%) of a bright orange precipitate, presumed to be the dihydrochloride salt. This was filtered and recrystallized from ethanol/water to give 0.3 grams of the dihydrochloride salt as an extremely hygroscopic brick-red powder. UV-vis (CHCl$_3$):408 nm; Anal. calcd for C50H34N4O2 . 2HCl . 2.5H$_2$O: C, 71.43%; H, 4.91%; N, 6.66%. Found: C, 71.51%; H, 4.70%; N, 6.50%.

Example 5

Preparation of N,N'[bis-4-oxy-1-phenylene]1,3-dimethyl-diphenyl propane-bis-[9-acridineamine Preparation was performed in analogous fashion to Example 1, condensing bis-[4-oxyaniline]-1,3-dimethyldiphenyl propane (0.42 grams, 1.02 mmol)with 9-chloroacridine (0.64 grams, 2.99 mmol) to yield 0.18 grams (23%) of a bright orange powder. NMR, UV, mass spec. and elemental analytical data support the structure assignment.

Example 6

Preparation of N,N'[bis-1,4-phenylene][1,4 bis 2,2'-dimethyl propane-1,4-phenyl bis[9-aminoacridine]

Preparation was performed in analogous fashion to Example 1, condensing N,N'[bis 1,4-phenylene]1,4-bis-2,2'-dimethyl propane-1,4-benzene (0.35 grams, 1.06 mmol) with 9-chloroacridine (0.94 grams, 4.40 mmol) to yield 0.55 grams (74%) of an orange powder. NMR, UV, mass spec., and elemental analytical data support the structure assignment.

Example 7

Preparation of N,N'[1,3-phenylenebis(oxy-3,1-phenylene]-bis[9-acridineamine]

Preparation was performed in analogous fashion to Example 1, condensing bis(1,3-oxyaniline)-1,3 benzene (0.06 grams, 0.21 mmol) with 9-chloroacridine (0.20 grams, 0.94 mmol) to yield 0.08 grams (60%) of an orange powder. NMR and mass spec. data support the structure assignment.

Example 8

Cytotoxicity Evaluation

L1210 murine leukemia cells were routinely maintained as suspension cultures in McCoy's 5A medium supplemented with 10% horse serum, glutamine, penicillin, and streptomycin and grown in a humidified environment of 10% carbon dioxide and 90% air at 37° C. Compounds were dissolved in dimethyl sulfoxide (DMSO) and 40 µg was added to 4 ml of L1210 cells (10$^5$ cells/tube) to attain final drug concentrations of 0.01, 0.1 and 10 µg/ml of culture. After 72 hours of continuous exposure to the drug, the cell concentration was determined by a Coulter counter (Model ZBF, Hialeah, Fla.). Growth inhibition was calculated for each drug concentration using the following formula:

% growth inhibition=(1−A)×100, wherein A=[cell # treated/cell # in DMSO alone].

The growth inhibition data were then used to calculate the ID50 value (the calculated drug concentration required to inhibit cell growth by 50% of control).

What is claimed is:

1. A compound having formula (I):

(I)

wherein Z is selected from a group consisting of

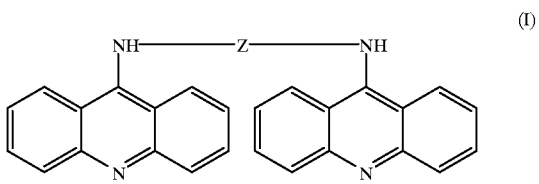

in either a cis-cis, cis-trans, or trans-trans configuration,

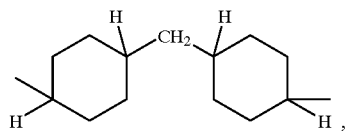

,

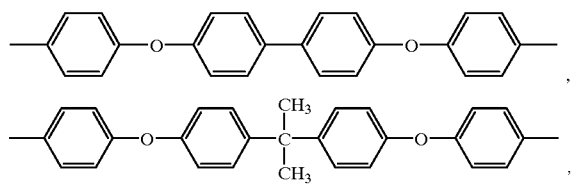

,

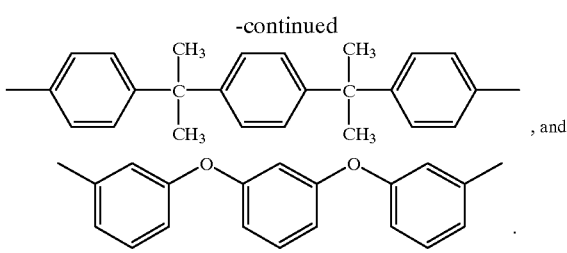, and

2. A pharmaceutical composition comprising a compound of claim 1 in a pharmaceutically acceptable carrier.

3. A method of inhibiting growth of leukemia cells comprising contacting leukemia cells with an effective amount of a compound of claim 1 so that growth of the cells is inhibited.

4. A method of treating leukemia comprising administering to a patient suffering from leukemia an effective amount of a composition of claim 2.

* * * * *